United States Patent [19]

Floyd, Jr.

[11] Patent Number: 5,166,369

[45] Date of Patent: Nov. 24, 1992

[54] PRECURSORS AND SYNTHESIS OF D1-(METHYL)-16,16-(DIMETHYL)-11-ALPHA, 15-ALPHA, BETA-DIHYDROXY-9-OXO-2,13,-TRANS, TRANS-PROSTADIENOATES

[75] Inventor: Middleton B. Floyd, Jr., Suffern, N.Y.

[73] Assignee: American Cyanamid Company

[21] Appl. No.: 570,219

[22] Filed: Aug. 21, 1990

Related U.S. Application Data

[60] Division of Ser. No. 371,686, Jun. 23, 1989, Pat. No. 4,983,753, which is a continuation of Ser. No. 633,240, Jul. 24, 1984, Pat. No. 4,644,079, division of Ser. No. 424,692, Sep. 27, 1982, Pat. No. 4,474,979, division of Ser. No. 266,004, May 21, 1981, Pat. No. 4,360,688.

[51] Int. Cl.$^5$ ............................................. C07D 307/54
[52] U.S. Cl. ..................................... 549/488; 549/501
[58] Field of Search ............................... 549/488, 501

[56] References Cited

U.S. PATENT DOCUMENTS

| | | | |
|---|---|---|---|
| 3,900,512 | 8/1975 | Sih | 560/121 |
| 3,931,296 | 1/1976 | Hayashi et al. | 560/121 |
| 4,024,174 | 5/1977 | Hayashi et al. | 560/121 |
| 4,061,670 | 12/1977 | Floyd, Jr. et al. | 560/121 |
| 4,069,387 | 1/1978 | Hayashi et al. | 560/121 |
| 4,076,732 | 2/1978 | Floyd | 549/488 |
| 4,087,620 | 5/1978 | Hayashi et al. | 560/121 |
| 4,190,596 | 2/1980 | Floyd, Jr. et al. | 560/121 |
| 4,197,245 | 4/1980 | Wissner | 560/121 |

OTHER PUBLICATIONS

March. Advanced Organic Chemistry, p.485 (1985).
Dunlop, Furans, pp. 421–424 (1953).
March. Advanced Org. Chem. pp. 892–893, 913, 1089 (1985).
March. Advanced Org. Chem. pp. 933–934 (1977).
Chen et al., J. Org. Chem. 43,3450 (1978).
K. Matsumoto, Abstract of the Fourth International Prostaglandin Conference, May 27–31, 1979, p. 77.
*Prostaglandins* 15, pp. 907–912 (1978).
Tsuboi, Arch. Int. Pharmacodyn 247, p. 89 (1980).
*Thrombus Research* 20, p. 573 (1980).

*Primary Examiner*—Robert Gerstl
*Attorney, Agent, or Firm*—Kenyon & Kenyon

[57] ABSTRACT

Novel compounds are disclosed of the derivatives of furan having the formula

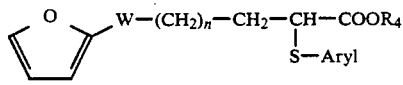

wherein $R_4$ consists essentially of hydrogen and $C_1$–$C_6$ alkyl, and W is either carbonyl or carbinol and N is from 3–5.

5 Claims, No Drawings

PRECURSORS AND SYNTHESIS OF D1-(METHYL)-16,16-(DIMETHYL)-11-ALPHA, 15-ALPHA, BETA-DIHYDROXY-9-OXO-2,13,-TRANS, TRANS-PROSTADIENOATES

This application is a division of Ser. No. 371,686 filed Jun. 23, 1989, now U.S. Pat. No. 4,983,753, which is a continuation of Ser. No. 633,240 filed Jul. 23, 1984, now U.S. Pat. No. 4,644,079, which is a division of Ser. No. 424,692 filed Sep. 27, 1982, now U.S. Pat. No. 4,474,979 which is a division of Ser. No. 266,004 filed May 21, 1981, now U.S. Pat. No. 4,360,688.

FIELD OF THE INVENTION

This invention relates to novel compounds useful as precursors in the synthesis of 1-(methyl)-16,16-(dimethyl)-11-alpha, 15-alpha-dihydroxy-9-oxo-2,13,trans,-trans-prostadienoate, congeners thereof, and racemic mixtures thereof. The compound named above has been described in the art to be useful for the induction of menses, for the induction of labor at term, and as an abortifacient; see the papers by K. Matsumoto, et al., which are referred to at p. 77 of the Abstracts of the Fourth International Prostaglandin Conference, May 27–31, 1979, and *Prostaglandins*, 15, 907–912 (1978). The compound has the structure

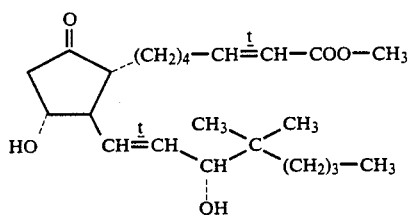

(11)

The invention also relates to novel processes of synthesizing new compounds, and from them, synthesizing the above-described prostadienoates, especially the compound of formula (11).

BRIEF SUMMARY OF THE INVENTION

The novel precursor compounds of this invention include the class of 2-aryl-thio alkane di-esters and mixed acid-esters represented by the formula

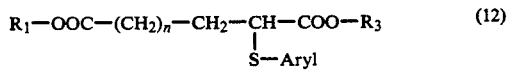

(12)

wherein the subscript n is an integer from 3–5 inclusive, $R_1$ is a monovalent radical selected from the class consisting essentially of hydrogen and $R_2$, wherein $R_2$ and $R_3$ are selected from the class consisting essentially of $C_1$–$C_6$ alkyl, and $R_2$ may be the same as or different from $R_3$, and wherein Aryl is selected from the class consisting essentially of phenyl and phenyl substituted with halogen, $C_1$–$C_4$ alkyl, $C_1$–$C_4$ alkoxy, and trifluoromethyl.

The various subscripts and symbols for chemical moieties, once defined herein, continue to have the same definition.

The novel precursor compounds also include the class of derivatives of furan represented by the formula

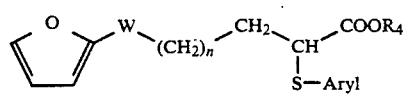

(13)

wherein $R_4$ is selected from the class of hydrogen, and $C_1$–$C_6$ alkyl, and wherein —W— is selected from the class consisting of a divalent carbonyl radical

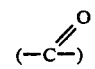

and a divalent carbinol radical (—CHOH—).

From the compounds of the preceding paragraph, one may obtain, by processes described herein, additional novel compounds which are cyclopentenones of the class represented by the formulas

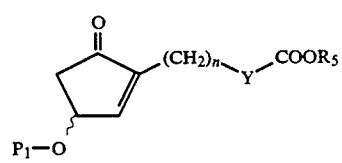

A

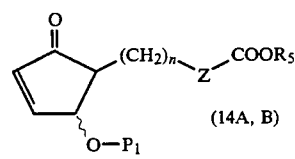

B (14A, B)

wherein $R_5$ is a monovalent radical selected from the class consisting essentially of hydrogen and $C_1$–$C_6$ alkyl, wherein —Y— is selected from the class consisting of a divalent unsaturated moiety (trans—CH=CH—) and a divalent aryl thio radical

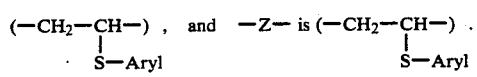

$P_1$ is a monovalent radical selected from the class consisting essentially of hydrogen or $P_2$. $P_2$ is a blocking or protective group which is stable under the conditions of the 1,4 conjugate addition process to which compound (14A, when Y is (trans-CH=CH—), is to be subjected, as described hereinafter, and which can thereafter be removed, usually by a mild acid treatment, without disruption of the prostaglandin product of which it forms a part. Such protective groups are well-known in the art and may be, for instance, tetrahydropyranyl, trialkylsilyl, such as trimethylsilyl or dimethyl-t-butylsilyl, or alpha-alkoxy ethyl.

When in compounds of formula (14A), $P_1$ and $R_5$ are each hydrogen, and Y is trans-CH=CH—, the compound is the racemic mixture of the 2-trans isomer of the 5-cis isomers of the compounds of formulas 23 and 24 depicted in U.S. Pat. No. 4,061,670, at column 12.

Broadly described, the novel processes of this invention include preparing compounds of formula (12), by reacting a 2-halo-alkanedioate diester with an alkali metal thio monocyclic aryl compound to form the 2-arylthio-alkanedioate diester. The ester radical which is less sterically hindered is then cleaved from the alkanedioate by hydrolysis, advantageously with a strong hydroxide, to form a mixed acid-ester. The latter is then reacted with an anhydride or an acyl halide to form a mixed anhydride, which in turn is reacted with furan to produce an acyl furan of the class of formula (13) when W is carbonyl. The carbonyl group is then reduced by reaction with a carbonyl reducing reagent, preferably a borohydride, to form a furyl carbinol of formula (13) when W is —CHOH—. The carbinol moiety is then subjected to an acid catalyzed re-arrangement and isomerization, and optionally esterification, to form, via the intermediate 3-hydroxy isomer (14B), the 4-hydroxy cyclopentenone compounds of formula (14A) wherein Y is a divalent aryl thio radical. The aryl thio radical is oxidized to an aryl sulfoxy radical and the 2-trans olefinic compound of formula (14A) (when Y is trans-CH=CH—) is formed by thermolysis with a peroxy organic acid.

The 4-hydroxy group of the cyclopentenone is then protected (for subsequent reactions) with an appropriate blocking group $P_2$.

It has been unexpectedly discovered that the beta-branch of prostaglandin-type compounds can then be added at the 3-cyclopentenonyl position of compounds of formula (14A) (in which Y is (trans-CH=CH—)) by reaction with a lithio-cuprate reagent, or a functional equivalent thereof, which is capable of furnishing a prostaglandin beta-chain having the formula

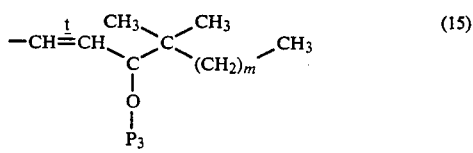
(15)

wherein $P_3$ is a monovalent protective group, to produce compounds having the formula

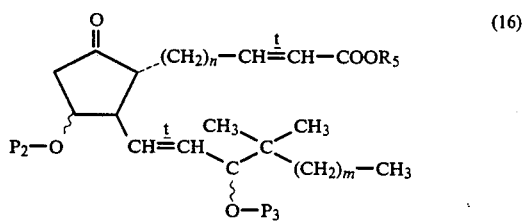
(16)

wherein m is an integer from 2-4 inclusive. Such lithio-cuprate reagents, or their functional equivalent, are disclosed in *J. Org. Chem.*, 43, 3450 (1978). Protective group $P_3$ should have the same characteristics described above in respect of $P_2$, and may be the same chemical moiety as, or may be different from, $P_2$.

The blocking groups $P_2$ and $P_3$ are then removed by hydrolysis to produce a racemic mixture. Where, in formula (16), n is 4, m is 3, and $R_5$ is methyl, the product of the foregoing comprises a mixture of 11-alpha-hydroxy, 15-alpha,beta-hydroxy isomers of the compound of formula (11). This mixture can be resolved by chromatography into the individual isomers, and dl-(methyl)-16,16-(dimethyl) 11-alpha, 15-alpha-(dihydroxy)-9-oxo-2,13-trans,trans-prostadienoate isolated therefrom.

The dotted lines shown in the formulas depicted herein indicate that the substituents are in the alpha configuration, i.e., below the plane of the cyclopentenonyl ring.

Many of the compounds described herein possess asymmetric centers and thus can be produced as racemic mixtures or as individual enantiomers. The racemic mixtures can be resolved if desired at appropriate stages by methods known to those skilled in the art, to obtain the respective individual enantiomers. It is to be understood that the racemic mixtures and the individual enantiomers are encompassed within the scope of the subject matter claimed herein.

DETAILED DESCRIPTION

The novel compounds disclosed herein may be prepared from a 2-halo-alkane diester having the formula

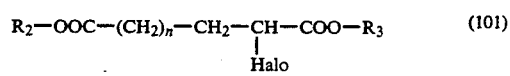
(101)

wherein the halo atom may be chlorine, bromine, or iodine. The 2-bromo-di-ethyl ester is taught in *Ber.*, 89, 51, (1956).

The overall process will be explained in conjunction with Flowchart A.

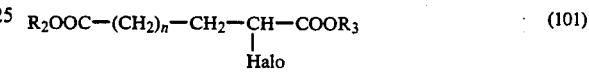
(101)

(102)

Step A    + (AM₁)—S—Aryl

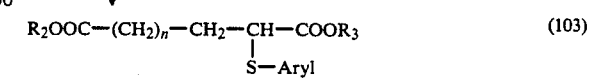
(103)

Step B    hydrolysis

(104)

(105A, B)

Step C

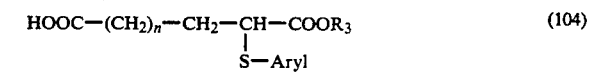

(106)

Step D    + furan

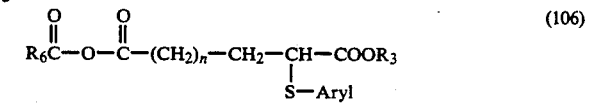
(107)

Step E    hydrolysis

(108)

Step F    carbonyl reducing reagent, e.g., borohydride

-continued

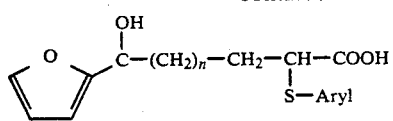

Step G-1 | weak acid, including an acidic phosphate buffer

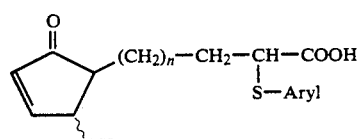

Step G-2 | sulfuric acid

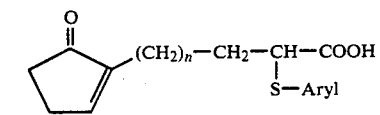

Step H | esterification

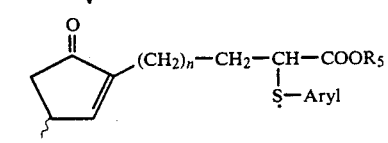

Step J | Peroxy organic acid; and thermolysis

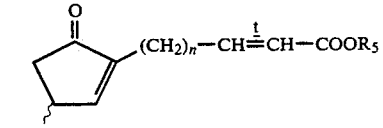

Step K | Blocking the hydroxyl moiety

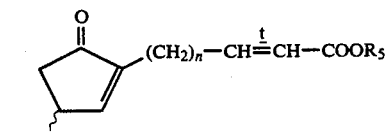

Step L | Conjugate addition with a lithio cuprate reagent, e.g.,

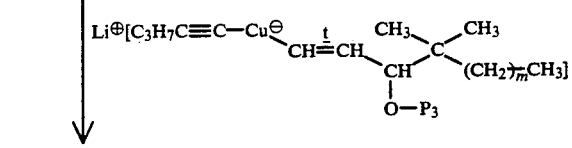

-continued

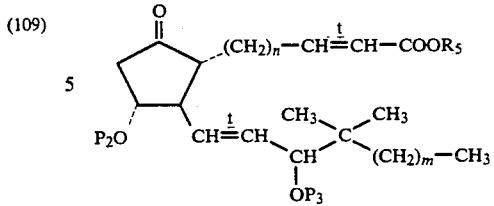

Step M | Hydrolysis of protecting groups

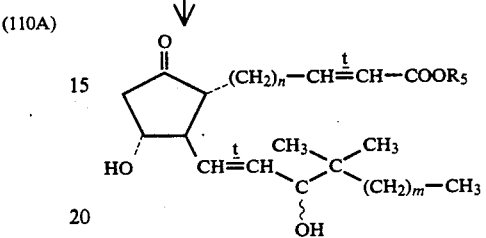

Step N | chromatographic resolution

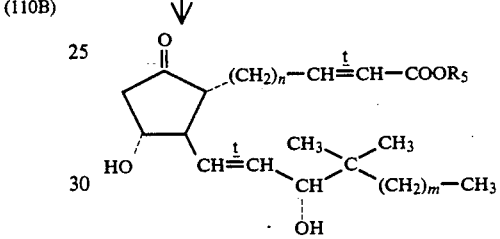

In accordance with Flowchart A, a 2-halo-diester of formula (101) is reacted, in Step A, with an alkali metal thioaryloxide to produce a 2-arylthio-alkanedioate of formula (103). The alkali metal ($AM_1$) may be any of sodium, potassium or lithium. The aryl moiety of the thioaryloxide is the same as the Aryl moiety defined above. The reaction is preferably conducted in an alcoholic solution.

The 2-arylthio compound of formula (103) is hydrolyzed in Step B to produce the monoester of formula (104), the lesssterically hindered ester moiety being cleaved. A strong hydroxide is preferred for the hydrolysis.

The monoester of formula (104) is reacted in Step C with an anhydride of formula (105A) or an acyl halide of formula (105B) to produce the mixed anhydride of formula (106). In the reactants of formulas (105A) and (105B), $R_6$ and $R_7$ are selected from the class consisting of $C_1$-$C_3$ alkyl and halo-substituted $C_1$-$C_3$ alkyl, and $R_6$ is preferably the same as but may be different from $R_7$. Advantageously a reactive anhydride such as ($F_3C-CO)_2O$ is employed.

The mixed anhydride of formula (106) is reacted in Step D with furan to produce a new class of acyl furan compounds of formula (107).

The compound of formula (107) is hydrolyzed in Step E, to form the acyl furan acid of formula (108).

The reactions of Steps C, D and E may optionally and advantageously be conducted in a single reaction zone without intermediate separation of the compounds of formulas (106) and/or (107).

The carbonyl moiety of formula (108) is reduced in Step F to a carbinol moiety to produce a new class of furyl carbinol compounds of formula (109), employing for the purpose a carbinol reducing reagent, such as a borohydride, e.g., sodium borohydride, in a solvent such as glyme. Preferably the reduction reaction of Step F is conducted in the presence of a salt of a weak acid, such as sodium carbonate or sodium acetate, to aid in the dissolution of the acyl furan of formula (108).

The furyl carbinol compound of formula (109) is then, in Step G, subjected to an acid catalyzed rearrangement to produce a racemic mixture of the isomers of formulas (110A) and (110B). The rearrangement is accomplished with an aqueous solution of a weak organic acid such as formic acid, or alternatively with an aqueous acidic phosphate buffer solution having a pH of about 3 (Step G-1). The resulting solution of 3-hydroxy (110A) and 4-hydroxy (110B) cyclopentenone isomers is then isomerized (Step G-2), advantageously in the same reaction zone, to the desired 4-hydroxy isomer of formula (110B) by the addition of a strong acid, such as sulfuric acid.

The compound of formula (110B) is then advantageously esterified by alkylation with, for instance, an alkyl halide ($R_5$—X) such as methyliodide, to form a compound of formula (111). Preferably, the alkyl moiety of such halide is selected to be the desired ester moiety ($R_5$) of the alpha-chain of the ultimately desired prostaglandin-type compound, e.g., a compound of formula (117).

The 2-arylthio moiety of formula (111) is removed and the 2,3-position carbons converted to a 2-trans double bond in Step J by reacting the compound of formula (111) with a peroxy organic acid in a suitable solvent to form an intermediate sulfoxide compound, which is then subjected to thermolysis (e.g., heated for an extended period at reflux temperature) until completion of the formation of a new class of 2-trans olefinic compounds of formula (112). The peroxy acid may be aliphatic or aromatic, and may be substituted, for example, peroxy acetic acid, peroxybenzoic acid or meta-chloroperoxybenzoic acid. The solvent may be a halogenated lower alkane such as dichloromethane.

The hydroxyl moiety of the compound of formula (112) is provided in Step K with a protective group $P_2$ capable of subsequently being easily removed without affecting the rest of the molecule, to form a compound of formula (113). Advantageously, $P_2$ is trimethylsilyl or tetrahydropyranyl.

A conjugate addition reaction is conducted in Step L by reacting a compound of formula (113) with a lithiocuprate addition reagent capable of furnishing a prostaglandin beta-chain having the formula (15), advantageously the reagent shown by formula (114), to produce a racemic mixture of compounds of formula (115).

Unexpectedly, the trans-CH=CH— moiety of the lithiocuprate reagent (15) or (114) adds to the 3-position of the cyclopentenonyl moiety of the compounds of formula (113), rather than to the alpha-side chain of formula (113).

The protecting groups $P_2$ and $P_3$ are then removed, and the hydroxy moieties re-created, by hydrolysis in Step M, employing, for instance, acetic acid, to produce a dl-racemic mixture of 15-alpha, beta-dihydroxy isomers of compounds of formula (116). Such mixture is then resolved by chromatography to isolate the desired isomers, which, when in formula (116) n is 4, m is 3, and $R_5$ is methyl, include the prostandionate of formula (11).

It should be understood that in the foregoing description of Flowchart A, the compounds of formulas (110A and B), (111), (112) and (113) are racemic mixtures of optically active isomers. At any desired point is the process sequence, any of such mixtures can be resolved by the application of known chromatographic techniques into the respective optically active isomers and the process sequence continued with either of the isomers alone. Likewise, the racemic mixture of compounds of formula (115) may be resolved before Step M, rather than after Step M, into the individual 15-alpha and 15-beta isomers. In separations conducted after Step M, such isomers may be obtained in their nat. configuration.

The compounds of this invention are also useful for the preparation of a compound of formula (118)

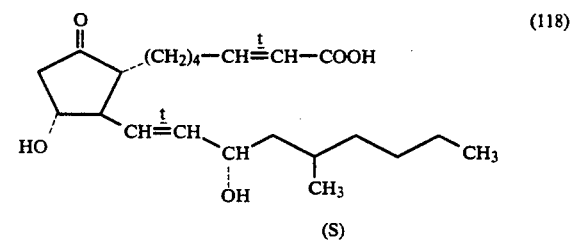

which is of potential use for the treatment of angina and as an inhibitor of blood platelet aggregation; see Tsuboi, et al., *Arch. int. Pharmacodyn.*, 247, 89 (1980) and *Thrombus Research*, 20, 573 (1980). The compound of formula (118) is prepared in the same manner as the compounds of formula (117) by substitution, for the reagent having the formula (114), of a compound having the formula:

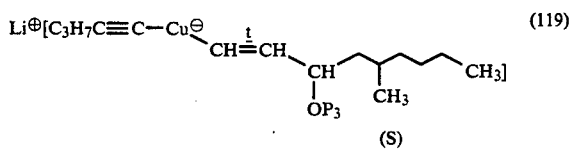

The invention will be described in greater detail in conjunction with the following examples.

EXAMPLE 1

Preparation of Diethyl-2-phenylthio-1,8-octanedioate

To a stirred solution of 175 ml. of 1.5M sodium ethoxide in ethanol at 0° C. is added to a solution of 29.8 g. of benzenethiol in 30 ml. of ethanol over 10 minutes. After 10 minutes this solution is treated with a solution of 79.5 g of diethyl-2-bromo-1,8-octanedioate (see. Ber., 89, 51, (1956)) in 70 ml. of ethanol during 15 minutes. The resulting mixture is stirred at ambient temperature for 60 minutes, then at reflux for 60 minutes, cooled to room temperature, treated with 3.0 ml. of glacial acetic acid and concentrated in vacuo. The residue is partitioned with water and ether. The ether layer is washed with water and brine, dried and evaporated. The residue is distilled to provide the product as a light yellow oily liquid, b.p. 165°-180° C. (0.15 mm Hg).

EXAMPLE 2

Preparation of Ethyl-7-carboxy-2-phenylthioheptanoate

To a stirred, ice-cold solution of 20.4 g. of diethyl-2-phenylthio-1,8-octanedioate in 100 ml. of ethanol is added dropwise a solution of 2.41 g. of sodium hydroxide in 12 ml. of water during 5 minutes. The resulting solution is maintained at 0° C. for 3.5 days and then at ambient temperature for 2 hours. The bulk of the ethanol is removed in vacuo and the residue is partitioned with ether and water. The aqueous layer is acidified with dilute hydrochloric acid and the acidic materials are extracted with ether. This extract is washed with water and brine, dried and concentrated. The residue is subjected to dry column chromatography on silica gel with 30:20:1 ethyl acetate-heptane-acetic acid providing the product as a light yellow oil. Its infra-red spectrum has peaks at 1735 and 1700 cm$^{-1}$.

EXAMPLE 3

Preparation of 8-(2-furyl)-8-oxo-2-phenylthiooctanoic acid

To a stirred, ice-cold solution of 7.75 g. of ethyl-7-carboxy-2-phenylthioheptanoate in 25 ml. of dichloromethane is added 3.5 ml. of trifluoroacetic anhydride during 2 minutes. The solution is stirred at ambient temperature for 10 minutes, recooled to 0° C. and treated with 9 ml. of furan during 2 minutes. The resulting solution is stirred at ambient temperature for 18 hours and then partitioned with 1:1 ether-petroleum either and aqueous sodium bicarbonate. The organic phase is washed with water and brine, dried and evaporated. The resulting crude ester (6.75 g.) is dissolved in 75 ml. of ethanol containing 4.95 g. of 85% potassium hydroxide and 10 ml. of water. This solution is refluxed for 20 minutes, cooled and concentrated in vacuo. The residue is partitioned with water and ether. The aqueous layer is acidified with dilute hydrochloric acid and extracted with ether. This extract is washed with water and brine, dried and evaporated, giving the product as an oil, identified as having a PMR$\delta$ 2.80 (2, t, J=7).

EXAMPLE 4

Preparation of 8-(2-Furyl)-8-hydroxy-2-phenylthiooctanoic acid

To a stirred solution of 3.61 g. of 8-(2-furyl)-8-oxo-2-phenylthiooctanoic acid, 5.45 ml. of 1M aqueous sodium carbonate, 25 ml. of water and 15 ml. of glyme is added 0.41 g. of sodium borohydride in portions during one minute. The resulting mixture is stirred at ambient temperature for 3.5 hours, diluted with ethyl acetate and acidified cautiously at 0°-10° C. with dilute hydrochloric acid. The organic layer is washed with water and brine, dried and evaporated, giving 3.54 g. of the product as an oil identified by its PMR $\delta$ 4.800 (1, t, J=7).

EXAMPLE 5

Preparation of 7-(4-Hydroxycyclopent-2-en-1-on-2-yl)-2-phenylthioheptanoic acid

To a stirred solution of 54.4 g. of 8-(2-furyl)-8-hydroxy-2-phenylthiooctanoic acid in 815 ml. of glyme and 610 ml. of water is added successively 0.5 g. of hydroquinone, 12.0 g. of sodium bicarbonate and 122 ml. of 90% formic acid. The resulting solution is heated at reflux temperature for 24 hours, cooled to 50° C. to produce a mixture of the 3-hydroxy and 4-hydroxy isomers. This is then treated dropwise with 40 ml. of concentrated sulfuric acid during 15 minutes. The resulting solution is refluxed for 18 hours, cooled, diluted with ethyl acetate and then saturated with sodium chloride. The organic layer is separated, washed with brine, dried and concentrated. The residue is subjected to chromatography on silica gel with chloroform progressively enriched in ether, giving 13.0 g. of the product as an oil, identified by its PMR$\delta$ 4.94 (1, broad s, C$\underline{H}$OH).

EXAMPLE 6

Preparation of Methyl 7-(4-hydroxycyclopent-2-en-1-on-2-yl)-2-phenylthioheptanoate A stirred mixture of 4.38 g. of 7-(4-hydroxycyclopent-2-en-1-on-2-yl)-2-phenylthioheptanoic acid, 1.99 g. of potassium carbonate, 1.63 ml. of iodomethane and 26 ml. of acetone is refluxed for 3.5 hours. The acetone is evaporated and the residue is partitioned between water and ether. The ether layer is washed with brine, dried and concentrated, giving the product as an oily liquid, identified by PMR$\delta$ 3.67 (3, s).

EXAMPLE 7

Preparation of Methyl 7-(4-hydroxycyclopent-2-en-1-on-2-yl)hept-2-trans-enoate

To a stirred, ice-cold solution of 5.20 g. of methyl 7-(4-hydroxycyclopent-2-en-1-on-2-yl)-2-phenylthioheptanoate in 50 ml. of dichloromethane is added a solution of 3.33 g. of 85% m-chloroperoxybenzoic acid in 100 ml. of dichloromethane during 45 minutes. After 2 minutes the mixture is treated with aqueous sodium sulfite and diluted with ether. The organic layer is separated, washed with sodium bicarbonate solution and brine and dried. The 5.5 g. of oil residue obtained an evaporation is dissolved in 150 ml. of glyme and heated at reflux for 5 hours. Evaporation of the solvent gives a crude product which is subjected to dry column chromatography on silica gel with 100:1 ethyl acetate-acetic acid, giving the product as a light yellow oily liquid, identified by PMR$\delta$ 5.75 (1,d, J=15, =C$\underline{H}$—CO).

EXAMPLE 8

Preparation of Methyl 7-(4-trimethylsiloxycyclopent-2-en-1-on-2-yl)hept-2-trans-enoate To a stirred mixture of 1.15 g. of methyl 7-(4-hydroxycyclopent-2-en-1-on-2-yl)hept-2-trans-enoate in 20 ml. of petroleum ether is added 1.2 ml. of bis(trimethylsilylacetamide). The solution which forms is allowed to stand at ambient temperature for 1.5 hours, then is diluted with petroleum ether, cooled to 0° C. and filtered. The crude product, obtained on concentration of the filtrate, is short path distilled, giving the product as a light yellow oily liquid, b.p. 145° C. (0.1 mm Hg).

EXAMPLE 9

Preparation of dl-Methyl 16,16-dimethyl-11-alpha, 15-alpha, beta-dihydroxy-9-oxo-2,13-trans, trans-prostadienoate To a stirred solution of 1.36 g. of 4,4-dimethyl-1-tri-n-butylstannyl-3-trimethylsiloxy-1-trans-octene in 2.4 ml. of tetrahydrofuran at −78° C. is added 1.25 ml. of 1.9M n-butyllithium in hexane. The solution is stirred at −40° C. for 60 minutes, cooled to −78° C. and treated with a solution of 0.34 g. of copper pentyne in 0.95 ml. of hexamethylphosphorous triamide and 6.0 ml. of ether. The solution is stirred at −78° C. for one hour and treated with a solution of 0.62 g. of methyl 7-(4-trimethylsiloxycyclopent-2-en-1-on-2-yl)hept-2-trans-enoate in 5.0 ml. of ether. The solution is stirred at −40° C. for 1.5 hours, treated at −78° C. with a solution of 0.3 ml.

of glacial acetic acid in 5.0 ml. of ether, diluted with ether and poured into a stirred mixture of 15 ml. of each of saturated ammonium chloride and 1N hydrochloric acid. The ether layer is washed with cold dilute hydrochloric acid, water and brine, then dried and evaporated, giving 2.14 g. of light yellow liquid. This liquid is treated with 20 ml. of 4:2:1 glacial acetic acid-tetrahydrofuran-water and the resulting mixture is stirred at 40° C. for 45 minutes, then diluted with toluene and evaporated to dryness in vacuo.

The tetrabutylstannane present in the resulting mixture is removed by passage as a heptane solution through 15 g. of silica gel. The mixture of prostadienoates is eluted from the silica gel with ethyl acetate. Evaporation of the ethyl acetate gives 1.06 g. of amber oil comprising a di-racemic mixture of the 11-alpha, 15-alpha,beta-dihydroxy compounds, the infrared spectrum of which has peaks at 1740, 1665 and 1020 cm$^{-1}$.

This oil is subjected to dry column chromatography on silica gel using the solvent 100:1 ethyl acetate-glacial acetic acid to provide the more mobile 15-beta epimer (147 mg.) and the less mobile 15-alpha-epimer (113 mg.) as light yellow oils.

Having thus described the invention, what is claimed is:

1. Compounds having the formula

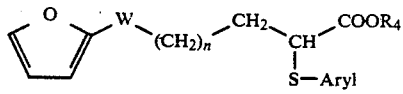

where n is an integer from 3-5 inclusive, $R_4$ is a monovalent radical selected from the class consisting of hydrogen and $C_1$-$C_6$ alkyl, Aryl is selected from the class consisting of phenyl and phenyl substituted with halogen, $C_1$-$C_4$ alkyl, $C_1$-$C_4$ alkoxy, or trifluoromethyl, and —W— is a divalent moiety selected from the class consisting of carbonyl

and carbinol

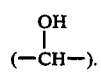

2. The compounds of claim 1, wherein n is 4 and Aryl is phenyl.

3. The compounds of claim 1, wherein Aryl is phenyl substituted with trimethylfluro.

4. The compounds of claim 1, wherein —W— is carbonyl.

5. The compounds of claim 1, wherein —W— is carbinol.

* * * * *